United States Patent
Barbucci et al.

(10) Patent No.: US 6,734,298 B1
(45) Date of Patent: May 11, 2004

(54) CROSS-LINKING PROCESS OF CARBOXYLATED POLYSACCHARIDES

(75) Inventors: Rolando Barbucci, Milan (IT); Giancarlo Sportoletti, Milan (IT)

(73) Assignee: Farmila-Thea Faraceutici S.p.A., Settimo Milanese (IT)

( * ) Notice: Subject to any disclaimer, the term of this patent is extended or adjusted under 35 U.S.C. 154(b) by 0 days.

(21) Appl. No.: 09/830,744

(22) PCT Filed: Nov. 9, 1999

(86) PCT No.: PCT/EP99/08480
§ 371 (c)(1),
(2), (4) Date: Jun. 18, 2001

(87) PCT Pub. No.: WO00/27886
PCT Pub. Date: May 18, 2000

(30) Foreign Application Priority Data

Nov. 11, 1998 (IT) .......... MI98A2443

(51) Int. Cl.⁷ .......... C08B 37/00
(52) U.S. Cl. .......... 536/55.1; 536/21; 536/55.2; 536/55.3; 514/54
(58) Field of Search .......... 536/55.1, 55.2, 536/55.3, 21; 514/54

(56) References Cited

U.S. PATENT DOCUMENTS

| | | | | |
|---|---|---|---|---|
| 4,582,865 A | * | 4/1986 | Balazs et al. | 514/781 |
| 4,605,691 A | * | 8/1986 | Balazs et al. | 524/27 |
| 4,636,524 A | * | 1/1987 | Balazs et al. | 514/781 |
| 4,713,448 A | * | 12/1987 | Balazs et al. | 435/267 |
| 4,716,154 A | * | 12/1987 | Malson et al. | 514/54 |
| 4,716,224 A | * | 12/1987 | Sakurai et al. | 514/825 |
| 4,772,419 A | * | 9/1988 | Malson et al. | 424/423 |
| 4,810,695 A | * | 3/1989 | Conti et al. | 514/55 |
| 4,957,744 A | * | 9/1990 | della Valle et al. | 424/401 |
| 5,676,964 A | * | 10/1997 | Della Valle et al. | 424/401 |

FOREIGN PATENT DOCUMENTS

| | | | | |
|---|---|---|---|---|
| EP | 0566118 A1 | * | 10/1993 | C08B/37/00 |
| EP | 0718312 A1 | * | 6/1996 | C08B/37/08 |

* cited by examiner

*Primary Examiner*—James O. Wilson
*Assistant Examiner*—Ganapathy Krishnan
(74) *Attorney, Agent, or Firm*—Walter H. Schneider

(57) ABSTRACT

A process for the preparation of cross-linked polysaccharides containg carboxy groups. The process comprises a first step of activating the carboxy groups in an anhydrous aprotic solvent and then reacting with a polyamine. The cross-linked polysaccharide may be subjected to sulfonation of the five hydroxy groups.

5 Claims, No Drawings

CROSS-LINKING PROCESS OF CARBOXYLATED POLYSACCHARIDES

The present invention refers to a cross-linking process of carboxylated polysaccharides.

The process of the invention provides a high degree of reproducibility of the obtained products, in terms of cross-linking degree, homogeneity of the distribution of the cross-linking chains, and chemico-physical characteristics of the products and the technological characteristics of the articles obtained therefrom.

The reproducibility is particularly important for the applications in the medical, pharmaceutical and dermo-cosmetic fields.

The invention further refers to the products obtainable by said process and their applications in the medical, pharmaceutical and dermo-cosmetic field.

BACKGROUND OF THE INVENTION

The use of macromolecules in the medical/pharrnaceutical field and, more recently, in the dermatological-cosmetic field, is well established. Macromolecules are used in the preparation of pharmaceutical formulations as thickening agents, lubricants, gastro-resistant film coating agents, particularly in the preparation of capsules, gel, colloids and of different devices (e.g. contact lenses, gauzes, etc.). Macromolecules are also used in the preparation of controlled-release formulations of active ingredients.

Reviews of their characteristics and pharmaceutical uses are reported in

1) C. Hansch et Al. Editors—"Comprehensive Medicinal Chemistry"—Pergamon Press, Oxford, 1990—Vol. 1–6;

2) A. Wade and P. J. Wellers Editors—"Handbook of Pharmaceutical Excipients"—Ed. 1994—The Pharmaceutical Press.

Said macromolecules belong to different chemical families and may be either synthetic, or natural or semi-synthetic.

Examples of synthetic macromolecules include polyvinylpyrrolidone, polyoxyethylenealkyl ethers, polyvinyl alcohols, polymethacrylates. Examples of natural macromolecules include native hyaluronic acid (HY) and cellulose.

Examples of semi-synthetic macromolecules include carboxyalkylcelluloses, widely used in the food and personal care industries. These macromolecules are characterized by a linear or poorly branched structure.

A very important modification for increasing the chemical, enzymatic and mechanical strength is provided by cross-linking, which may be carried out both on synthetic and natural (more or less already modified) polymers.

Examples of cross-linked polymers include polymers used for the gastro-protection of tablets or capsules (polymethacrylates), as well as polymers used as emulsifiers, suspending agents, tablet hardeners (Carbopol), cross-linked hyaluronic acids, hereinafter discussed.

For the considered applications, and particularly for the preparation of invasive medical devices which have to be administered parenterally, said polymers must meet a number of requirements, of technical and regulatory kind.

The technical requirements include:

1) high biocompatibility;

2) resistance to enzymatic systems, both tissular or plasmatic (for injectable compositions) and gastrointestinal (for oral compositions).

In some cases a gradual degradation, for instance for the controlled release of a medicament, may be desirable.

This resistance is particularly important when the macromolecule is present in compositions/articles that must last for a long time, e.g. substitutes of the synovial liquid, films, sponges or gels as tissular antiadhesives in different kinds of surgery; in tissular engineering (artificial organs); artificial skins, in the treatment of burns and generally in aesthetic surgery;

3) moldability into different shapes (gels, films, sponges, etc.);

4) possibility to be sterilized chemically or physically without changing the product structure.

According to the regulatory requisites, the composition of the different production batches must be kept constant within very narrow limits; this implies that the production methods are standardized and that the base components have a very low intrinsic variability.

A possible cause of dishomogeneity for macromolecules derives from the dispersion of molecular weights. Said dishomogeneity becomes even higher as a consequence of cross-linking. This may be a serious drawback depending on the field of use and the applicative purposes of the final product.

EP-A-566118 (Kimberly-Clark) discloses cross-linked polysaccharides to be used as super-absorbents for diapers and similar articles.

The process described therein is based on the cross-linking of cellulose by formation of intermolecular amides, esters or ethers between polyamines, polyols or mixtures thereof and the carboxy group of polysaccharides.

The reaction is carried out by heating at about 80° C. the mixture of the polysaccharide with the polyol and/or polyamine. This process is certainly economic and suitable for large scale production where the reproducibility requirements are less stringent.

U.S. Pat. No. 5,465,055 discloses cross-linked polysaccharides (hyaluronic acid and alginic acid) obtained by esterification of COOH of the polysaccliaride and OH groups of other molecules, without insertion of cross-linking arms.

WO 91/9119 discloses microcapsules for islets of Langerhans as biohybrid organs, consisting of alginic acid cross-linked with barium ions.

EP 190215 discloses the cross-linking of different polymers (carboxylated starches, dextran, celluloses) with di- or poly-functional epoxides.

The following cross-linking agents for hyaluronic acids have been proposed:

polyfunctional epoxides are disclosed in U.S. Pat. Nos. 4,716,224, 4,772,419, 4,716,154;

polyalcohols are disclosed in U.S. Pat. No. 4,957,744;

divinylsulfone is disclosed in U.S. Pat. Nos. 4,605,691, 4,636,524;

aldehydes are disclosed in U.S. Pat. Nos. 4,713,448 and 4,582,865;

carboxamides are disclosed in U.S. Pat. No. 5,356,833;

polycarboxylic acids are disclosed in EP-A-718312.

DISCLOSURE OF THE INVENTION

The invention refers to a process for the preparation of cross-linked polysaccharides containing carboxy groups, allowing complete control of cross-linking degree as well as high reproducibility in terms of constant characteristics of the final product.

The process of the invention comprises:
a) activation of the carboxy groups of the polysacchatide by reaction with suitable carboxy activating agents in anhydrous aprotic solvent;
b) reaction of the carboxy activated polysaccharide with a polyamine.

The obtained cross-linked polysaccharide, if desired, may be subjected to sulphation or hemisuccinylation of the free hydroxy groups.

The products obtainable by the process of the invention may also be complexed with metal ions such as zinc, copper or iron ions.

The carboxy-containing polysaccharide which may be used according to the invention may be of natural, synthetic or semi-synthetic origin. Examples of said polysaccharides include Hyaluronic acids (obtained from tissues or bacteria), carboxymethyldextran, carboxymetbylcellulose, carboxymethyl-starch, alginic acids, cellulosic acid, N-carboxy-methyl or butyl glucans or chitosans; heparins with different molecular weights, optionally desulphated and succinylated, derrnatan sulphates, Chondroitin sulphates, heparan sulphates, polyacrylic acids.

Hyaluronic acids, carboxymethylcellulose, heparins, alginic acids and polyacrylic acids are particularly preferred.

Said cross-linked polymers, obtained by different methods, are known and have been proposed for several uses (see, for instance, EP 566118, WO91/9119, U.S. Pat. Nos. 5,465,055, EP 190215, EP 718312, U.S. Pat. Nos. 4,716,224 discussed above).

The carboxy activating agents are usually those used in the peptide chemistry: examples of suitable agents include carbonyldiimidazole, carbonyltriazole, chloromethylpyridylium iodide (CMP-J), hydroxybenzotriazole, p-nitrophenol p-nitropheriyltrifluoroacetate, N-hydroxysuccinimide and the like. The use of chloromethylpyridylium iodide is particularly preferred.

The polyamines have preferably the following general formula:

$$R_1-NH-A-NH-R_2$$

wherein $R_1$ and $R_2$, which are the same or different, are hydrogen, $C_1$–$C_6$ alkyl, phenyl or benzyl groups, A is a $C_2$–$C_{10}$ alkylene chain, preferably a $C_2$–$C_6$ alkylene chain, optionally substituted by hydroxy, carboxy, halogen, alkoxy, amino groups; a polyoxyalkylene chain of formula $$[(CH_2)_n-O-(CH_2)_n]_m$$

wherein n is 2 or 3 and m is an integer from 2 to 10; a $C_5$–$C_7$ cycloalkyl group; an aryl or hetaryl group, preferably 1,3 or 1,4-disubstituted benzene. A is preferably $C_2$–$C_6$ linear alkylene or a chain of formula $$[(CH_2)_n-O-(CH_2)_n]_m$$

The cross-linking reaction is preferably carried out in a solvent selected from tetrahydrofuran, dimethylformamide or dimethyl sulfoxide, and the polysaccharide is preferably salified with a lipophilic cation, for example tetralkylammonium or other lipophilic organic bases.

The transformation of inorganic salts such as sodium salts, into suitable organic lipophilic salts may be carried out by known ion-exchange methods in homogeneous phase or by precipitation of the acidic component, followed by recovering of the latter and salification with the desired organic base.

The activation reaction of the carboxy groups is carried out in homogeneous phase and in anhydrous polar aprotic solvent.

The polyamine diluted in the same anhydrous solvent, is added to the solution of the activated ester, keeping the temperature from 0° C. to 30° C. The cross-linking reaction times range from 1 to 12 hours, also depending on the optional presence of suitable basic substances (e.g. triethylamine).

Generally, the final product is recovered by precipitation of the organic salt adding a different solvent to the reaction solvent or by evaporation of the latter, followed by centrifugation, washing with distilled water, repeated dispersions in the solutions of the desired alkali (for instance sodium, potassium), subsequent washing with water and final drying of the alkaline salt under vacuum or by lyophilization.

The cross-linking degree (C.L.D) may range within wide limits and may be adjusted by changing the amount of the carboxy activating agents, since the activation and the cross-linking reaction are substantially quantitative.

The cross-linked polysaccharides obtained according to the invention may be subjected to sulphation reaction of the hydroxy groups possibly present, usually by reaction with the pyridine-sulfur trioxide complex in dimethylformamide.

The reaction is carried out in heterogeneous phase at a temperature of 0–10° C. for times ranging from about 0,5 to about 6 hours.

The sulphation degree obtained is comprised within wide limits with respect to the total of the hydroxy groups and it may be adjusted by changing the temperature and reaction times. Generally, the sulphation degree (defined as equivalents of sulphate groups/g) may range from $1 \times 10^{-6}$ to $6 \times 10^{-6}$, preferably it is of $2 \times 10^{-6}$ eq/g for a cross-linking degree of 0.5.

The cross-linked polymers obtained according to the invention, optionally sulphated, are able to complex metal ions such as zinc, copper or iron ions.

Said complexes may be obtained by dissolving or dispersing until complete swelling the product in water and adding under stirring, preferably at room temperature, a concentrated solution of an organic or inorganic metal salt, e.g. $CuCl_2$, $ZnCl_2$, $Fe_2(SO_4)$; after stirring for 12–24 hours, the complex is recovered by centrifugation or by precipitation following the addition of a different solvent (for example ethanol or acetone) or evaporation under vacuum; the recovered crude product is thoroughly washed with distilled water so as to remove the excess ions. The complexes are then lyophilized. The content of metal ions varies depending on the used operative conditions, particularly the polymer to ion molar ratios; concentration and pH of the solutions; reaction times and particularly cross-linking degree.

The process of the invention, by suitably adjusting the cross-linking and/or sulphation degree, allows the preparation of cross-linked carboxylated polysaccharides in a wide range of shapes, characterized by different properties such as viscoelasticity, hydration degree, complexing ability towards metal ions, ability to form hydrogels, moldability in films or sponges, mechanical strength of the final materials.

This allows their use in many medical fields, in the human and veterinary field, and in dermo-cosmetology.

The following examples further illustrate the invention.

EXAMPLE 1

Carboxymethylcellulose gel 100% cross-linked with 1,3-diaminopropane.

$1,2 \times 10^{-3}$ moles, with reference to the disaccharide unit of carboxymethyl cellulare TBA salt, were dissolved in 30 ml of DMF under $N_2$ and with stirring. 0.32 g of chloromethylpyridylium iodide ($1.2 \times 10^{-3}$ moles) dissolved in 2 ml of DMF were added dropwise to the solution kept at a temperature of 0° C. with ice.

The molar ratio was 1 to 1 as carboxymethyl cellulose has one functional carboxylic group per disaccharide unit. After 20 minutes the solution was added with 2 ml of cross-linking 1,3-diaminopropane (0.006 moles), and immediately after also with 0.5 ml of triethylamine. A solid, jelly-like product formed which was washed with DMF, then placed in $H_2O$ to completely swell.

Alternating washings with EtOH and $H_{2O}$ were then carried out. After the last washing with EtOH, the product was freeze-dried.

I.R. (film; $cm^{-1}$): 1650(—CO—NH—); no bending — COO$^-$ at 1.400 about.

SD (Swelling Degree, in water and r.t., after 15'; gravimetric determination; calculated according to:

$$SD = \frac{W_s - Wd}{Wd} \cdot 100,$$

where:

$W_s$=weight of hydrated gel; Wd=weight of dry gel): 7.000
SEM (Scanning Electron Microscopy): the structure looks compact, with 15–35 μpers.

The product surface, by rabbit PRP (Platelet Rich Plasma) exposure, shows a very reduced presence of platelets or aggregates in comparison with equivalent product obtained by low density polypropylene (EC reference standard).

EXAMPLE 2

Carboxymethyl cellulose gel 50% cross-linked with 1,3-diaminopropane.

$1.2 \times 10^{-3}$ moles, referred to the disaccharide unit of carboxymethyl cellulose, were dissolved in 30 ml of DMF under $N_2$ and with stirring. 0.24 g of chloromethylpyridylium iodide ($1.2 \times 10^{-3}$ moles) dissolved in 2 ml of DMF were added dropwise to the solution kept at a temperature of 0° C. with ice. The molar ratio was 2/1.

After 20 minutes the solution was added with 2 ml of cross-linking 1,3-diaminopropane ($3 \times 10^{-3}$ moles), and immediately after also with 0.5 ml of triethylamine. A solid, jelly-like product formed which was washed with DMF, then placed in $H_2O$ to completely swell.

Alternating washings with EtOH and $H_2O$ were then carried out. After the last washing with EtOH the product was freeze-dried.

I.R. (film; $cm^{-1}$): 1650(—CO—NH—); no bending — COO$^-$ at 1.400 about.

SD: 8.000.

SEM: presence of 13–25 μpers.

Platelet adhesion: as reported in Example 1.

EXAMPLE 3

Alginic acid gel 50% (100% with reference to disaccharide units) cross-linked with 1,3-diaminopropane.

The TBA salt of alginic has been prepared from the sodium salt by ionic exchange on strong cationic resin (Dovex) in H$^+$ form (i.e. acidic form), followed by neutralization with tetrabutylammonium hydroxide (TBA—OH) and final liophylisation.

$1.2 \times 10^{-3}$ moles, refered to the monosaccharide unit, were dissolved in 30 ml of DMF under $N_2$ and under stirring. 0.36 g of chloromethylpyridylium iodide ($1.2 \times 10^{-3}$ moles) dissolved in 2 ml of DMF were added dropwise to the solution kept at a temperature of 0° C. with ice. The molar ratio was 1/1.

After 20 minutes the solution was added with $6 \times 10^{-3}$ moles of cross-linking 1,3-diaminopropane (0.024 moles), and immediately after also with 0.5 ml of triethylamine. A solid, jelly-like product formed which was washed with DMF, then placed in $H_2O$ to completely swell.

Alternating washings with EtOH and $H_2O$ were then carried out. After the last washing with EtOH the product was freeze-dried.

IR (film; $cm^{-1}$): 1635 (broad) (—CO—NH—): 1.400, about (—COO$^-$).

SD: 5.000.

SEM: the structure looks compact and without pores.

EXAMPLE 4

Preparation of hyaluronic acid cross-linked with C.L.D.= 0.05 (5% of available carboxy groups). Cross-linking agent: 1,3-propanediamine.

Hyaluronic acid sodium salt ($1 \times 10^{-3}$ mol., with reference to the disaccharidic unit) were transformed in TBA salt, according to one of the following methods:

a) 1% aqueous solution of sodium hyaluronate is transformed in H$^+$ form by H$^+$ cationic strong resin (Amberlite IR 120); the final solution is treated by a 0,5% solution of TBA—OH to about pH=9.

b) 1% aqueous solution of sodium hyaluronate is transformed in TBA salt solution by treating with a cationic weak resin in TBA$^+$ form. (Amberlite IRC 50)

In both cases, the final solutions are liophylised. The TBA salt is then dissolved in 15 ml of anhydrous DMF, under $N_2$, and—at 0° C.—0,02 g of cloromethypyridylium Iodide (CMPJ) in 2 ml of anhydrous DFM, are added dropwise to the stored solution of TBA salt.

The reaction mixture was then added with 0.1 ml of triethylamine and, then, dropwise, with a solution of 1,3-diaminopropane (d=0.88, in large excess, so as to make cross-linking of the activated carboxy groups easier) in 2 ml of anhydrous DMF. When the addition was over, the reaction mixture was stirred for at least 30' and the solvent was then removed under reduced pressure, the residue was then taken up with DMF, which was subsequently removed by distillation; the residue was then treated with ethanol, ethanol-water and finally with water.

The product was then lyophilised and the residue subjected to analysis.

IR (film; $cm^{-1}$): 1630 (—CO—NH); 1740 (—COOH, polysaccharide); 3200 (—NH—).

SD (Swelling Degree, in water and r.t., after 15'; gravimetric determination; calculated according to:

$$SD = \frac{W_s - Wd}{Wd} \cdot 100,$$

where:

$W_s$=weight of hydrated gel; Wd=weight of dry gel): 31.000 Cross-linking degree: 0.05 (5% of initially available carboxy groups).

EXAMPLE 5

Preparation of hyaluronic acid cross-linked with C.L.D.= 0.05 (5% of the available carboxy groups). Cross-linking agent: 1,6-diaminohexane.

Activator: chloromethylpyridylium iodide.

According to the procedure and conditions reported in Example 4, using the same HY and the same activator, but 1,6-diaminohexane instead of 1,3-diaminopropane, the cross-linked derivative was obtained.

IR (film; cm$^{-1}$): 1630 (—CO—NH); 1740 (—COOH polysaccharide); 3200 (—NH—).

EXAMPLE 6

Preparation of cross-linked hyaluronic acid, with C.L.D.= 0.05 (5% of the available carboxy groups). Cross-linking agent: 0.0'-bis-(2-aminopropyl)PEG500. Activator: chloromethylpyridylium iodide According to the procedure and conditions reported in Example 4 and using the same activator, but 0.0'-bis-(2-aminopropyl)PEG500 instead of 1,3-diaminopropane, the cross-linked derivative was obtained. IR (film; cm$^{-1}$): 1630 (—CO—NH); 1740 (—COOH polysaccharide); 3200 (—NH—).

SD: 31.000.

EXAMPLE 7

Preparation of cross-linked hyaluronic acids, with C.L.D.=0.3 (30% of the available carboxy groups). Cross-linking agent: 1,3-propanediamine. Activator: chloromethylpyridylium iodide.

0.6 g of hyaluronic acid tributylammonium salt (1×10$^{-3}$ mol., with reference to the disaccharide unit) were dissolved under stirring in 30 ml of DMF under nitrogen. 0.08 g of chloromethylpyridylium iodide (3.5×10$^{-4}$ mol) dissolved in 2 ml of DMF were added dropwise to the stirred solution kept at 0° C. The molar ratio was therefore about 3/1.

After 20 minutes 2 ml of 1,3-diaminopropane (0.024 mol) were added, followed immediately by 0.5 ml of triethylamine. A solid, gelatinous product was obtained, the product was then swelled with water and washed again with ethanol.

The final product, after lyophilisation, shows at the scanning microscope an irregular pattern with smooth zones alternating to spongy zones.

The cross-linking degree was 0.3 (30% of initially available carboxy groups)

IR (film; cm$^{-1}$): 1740 (—COOH); 1630 (—CO—NH); 1610 (—COO—); 1560 (—CO—NH—).

EXAMPLE 8

Preparation of hyaluronic acid cross-linked with C.L.D.= 0.5 (50% of the available carboxy groups). Cross-linking agent: 1,3-propanediamine. Activator: chloromethylpyridylium iodide.

0.6 g of hyaluronic acid tributylammonium salt (HY TBA) (1×10$^{-3}$ mol., with reference to the disaccharide unit) were dissolved under stirring in 30 ml of DMF under nitrogen. 0.15 g of chloromethylpyridylium iodide (CMPJ) (6×10$^{-6}$ mol) dissolved in 2 ml of DMF were added dropwise to the solution, kept at 0° C. The molar ratio was 2HY.TBA:1 CMPJ. After 20 minutes, 2 ml of 1,3 diaminopropane (0.024 mol.) were added to the solution.

0.5 ml of triethylamine were added thereafter.

A solid, gelly-like product was obtained and thoroughly washed with DMF.

After evaporating DMF, the product was swelled in water and washed with ethanol before lyophilization.

The obtained product had a cross-linking degree of 0.5 and showed at the scanning microscope a grainy aspect interspaced by large meshes. At higher magnifications, the two morphologies appear identical and show round-shaped protrusions a few microns in diameter.

IR (film; cm-1): 1740 (—COOH); 1630 (—CO—NH—); 1610 (—COO—); 1560 (—CO—NH—);

The gels were subjected to swelling in PBS and the max swelling ability was evaluated.

SD=23.500.

NMR=(13 C; ppm): 29.3 and 39.8 (—CH$_2$—CH$_2$—CH$_2$— propanediamine link); 172.5

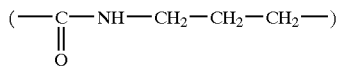

The rheological properties evaluated on Bohlin VOR Rheometer, at the temperature of 23=0.1° C., show that the dynamic elastic module G' (100 Pa at 10 Hz) identical at the two considered concentrations (10 and 20 mg/ml) is always higher than the viscous dynamic module (G" 40 Pa for 20 mg at 10 Hz and 20 Pa for 10 mg at 10 Hz).

EXAMPLES 9–12

According to the methods disclosed in the previous examples, the cross-linked hyaluronic acid derivatives having the characteristics summarised in the following table 1, were obtained, starting from 1×10$^{-3}$ mol (0.6 g) of hyaluronic acid tributylammonium salt.

The obtained derivatives had the following properties:

TABLE 1

| Ex | Cross-linking agent (mol) | Amount (g) of CMPJ (mol) | Cross-linking degree | SD | NMR (13) (ppm) | I.R. (film) (cm$^{-1}$) | Scanning Electron Microscopy (SEM) |
|---|---|---|---|---|---|---|---|
| 9 | 1,3-propanediamine (0.024) | 0.6 g (1.210$^{-3}$) | (100%) | 13.200 | 29.3/39.8 (—CH$_2$—CH$_2$—CH$_2$— propanediamine link); 172.5 (—C(=O)—NH—CH$_2$—CH$_2$—CH$_2$—) | 1630 (—CO—NH—); 1560 (—CO—NH—); | Homogeneouns, ondulated morphology. |
| 10 | 0,0'-1-bis-(-2-diaminopropyl) PEG 500 (0.022) | 0.15 g (6 × 10$^{-4}$) | (50%) | 9.000 | | | Alternating smooth areas and meshes, circular |

TABLE 1-continued

| Ex | Cross-linking agent (mol) | Amount (g) of CMPJ (mol) | Cross-linking degree | SD | NMR (13) (ppm) | I.R. (film) (cm$^{-1}$) | Scanning Electron Microscopy (SEM) |
|---|---|---|---|---|---|---|---|
| 11 | 0,0'-bis (2-aminopropyl)-PEG 800 (0.022) | 0.15 g (6 × 10$^{-4}$) | (50%) | 6.100 | | | protrusions a few microns in size. Two morphologically different zones, a first one ondulated and a second with hole-like structures. |
| 12 | 1,6-diaminohexane (0.023) | 0.15 g (6 × 10$^{-4}$) | (50%) | 8.000 | 169.46 (—CO—NH— of cross-linking); 74.04/76.80/83.17/80.41 (—CH2— of cross-linking arm) | 1740 (—COOH); 1630 (—CO—NH—); 1610 (—COO); 1560 (—CO—NH—); | Smooth surface with protrusions having a few microns in size. |

EXAMPLE 13

Sulphation of 50% Cross-linked HY

The derivative obtained in example 8 was dispersed in 5 nil DMF under strong stirring and nitrogen atmosphere.

A solution of 1 g of SO$_3$/pyridine in mol of DMF was added at 0° C. and stirred for 3 hours. The reaction was blocked by adding an excess of H$_2$O (50 ml) and the pH adjusted to 9 with 0.1M NaOH.

The product was thoroughly washed with ethanol and H$_2$O and then lyophilized.

The IR spectrum shows, in addition to the bands of the starting product, a peak at 1260 cm$^{-1}$ and a stronger band at 1025 cm$^{-1}$.

The gel swells in PBS with SD=33.000. Higher resolution 13C NMR spectrum shows the signals in H$_2$O at 37° C. reported in table 2. The intensity of the NMR signals at 29.3 and 38.8 ppm (—CH$_2$—) and the signal at 172.5 ppm (CONH) confirm a cross-linking degree of about 50%.

The rheological properties are characterised by dynamic elastic modules G' (2500 Pa with 20 mg and 1000 Pa with 10 mg at 10 Hz) which are always higher than the dynamic viscous modules G" (600 Pa with 20 mg and 150 Pa with 10 mg at 10 Hz) and much higher than the corresponding values obtained with non-sulphated HY (13 at 50%—example 5). This compound has a thrombin time (TT) higher (61±5") than the control (14.0") and the corresponding not cross-linked (14.6").

The compound was also active in the PRP test using stressed rabbit.

TABLE 2

Table: 13C Chemical shift

| C-1 | C-2 | C-3 | C-4 | C-5 | x-C=O | y-CH$_3$ | |
|---|---|---|---|---|---|---|---|
| 103.5 | 57.3 | 85.4 | 71.3 | 78.7 | 178.0 | 25.3 | ppm |
| C-1' | C-2' | C-3' | C-4' | C-5' | 6-C=O | | |
| 105.9 | 75.2 | 76.4 | 82.8 | 78.6 | 176.2 | | ppm |
| 1-CH2 | 2-CH2 | 3-CH2 | 6'-C=O | | CROSS-LINKING | | |
| 39.8 | 29.3 | 39.8 | 172.5 | | | | ppm |

EXAMPLE 14

Sulphation of Alginic Acid GEL

The cross-linked product after treatment with EtOH was freeze-dried to remove completely humidity and subjected to sulphation of the alcohol groups.

100 mg of cross-linked product dispersed in 5 ml of DMF were added with a SO$_3$-pyridine solution of (800 mg in 2 ml of DMF). The reaction should be carried out at 0° C., under nitrogen and with constant stirring for 2 hours.

It is mandatory for the product not to adsorb humidity, as it inhibits the reaction.

After 2 hours H$_2$O was added pH was adjusted to 9 by a 1M solution of NaOH, thereby freeing pyridine.

The thus sulphated product was purified in EtOH.

The analysis of purified products, shows:

IR (film; cm$^{-1}$) 1263 (stretching SO)

Equivalents of SO$_3$ groups/g gel (by toluidine complexes):

5% cross linked gel: 6×10$^{-5}$
50% cross linked gel: 2×10$^{-5}$
100% cross linked gel: 3×10$^{-5}$
SD
5% cross linked gel: 19×10$^3$
50% cross linked gel: 9×10$^{-3}$
100% cross linked gel: 7×10$^{-3}$

EXAMPLE 15

Using the same methodology, the sulphated derivatives of 50% cross-linked products according to example 10,11 and 12, have been synthetized.

Colorimetric characteristics of the sulphated derivatives are reported in table 3 together with that of the products deriving from examples 8 and 13.

TABLE 3

| CROSSLINKED POLYMER (50% CROSS-LINKING DEGREE) | ΔHa [J/g] | Tg [° C.] | ΔHb [J/g] | Wt % water |
|---|---|---|---|---|
| C.L. Hyal - 1,3 (Ex. 8) | 276 | 51 | 42 | 12 |
| C.L. HyalS - 1,3 (Ex. 13) | 357 | 64 | 53 | 16 |
| C.L. Hyal - 1,6 (Ex. 12) | 327 | 64 | 58 | 16 |
| C.L. HyalS - 1,6 | 465 | 64 | 65 | 20 |
| 5 C.L. Hyal - P500.2NH$_2$ (Ex. 10) | 239 | 45 | 72 | 10 |
| 6 C.L. HyalS - P500.2NH$_2$ | 384 | 69 | 113 | 16 |
| 7 C.L. Hyal - P800.2NH$_2$ (Ex. 11) | 179 | 73 | 30 | 10 |
| 8 C.L. HyalS - P800.2NH$_2$ | 206 | 76 | 52 | 10 |
| Hyal ITBA | 164 | — | 130 | 5 |

ΔHa [J/g]: water vaporization henthalpy
Tg [° C.]: enthalpy for thermal degradation process
ΔHb [J/g]: glass transition temperate
Wt % water: % of water content, based on ΔHa

EXAMPLE 16

Suphation of carboxymethylcellulose gel.

Following the procedure and conditions reported in Example 14, the sulphated derivative was obtained.

Equivalents of SO$_3$ groups/g:

a- CMC 5% cross linked: $8 \times 10^{-6}$ b- CMC 50% cross linked: $7 \times 10^{-6}$ c- CMC 100% cross linked: $4 \times 10^{-6}$

SD a: $20 \times 10^3$ b: $12 \times 10^{-3}$ c: $9 \times 10^{-3}$

What is claimed is:

1. A process for the preparation of cross-linked polysaccharides wherein the cross-linking occurs only through amide bonds between carboxy groups of the starting polysaccharides and amino groups of a polyamine in which the polysaccharide is selected from the group consisting of hyaluronic acids, carboxymethyldextran, carboxymethylcellulose, carboxymethylstarch, alginic acids, cellulose acid, N-carboxy-methyl or butyl glucans or chitosans, heparins with different molecular weights, optionally desulphated and succinylated, dermatan sulphate, chondroitin sulphates and heparan sulphates comprising (a) activating the caboxy groups of the polysaccharide in an aqueous aprotic solvent using a suitable carboxy activating agent; (b) reacting the carboxy activated polysaccharide with a polyamine selected from the group having the formula R1—NH—A—NH—R2 wherein R1 and R2, which may be the same or different, are hydrogen, C 1–C6 alkyl, phenyl or benzyl groups; A is a C2–C10 alkylene chain; a polyoxyalkylene chain of the formula [(CH$_2$)$_n$—O—CH$_2$)$_n$]m wherein n is 2 or 3 and m is an integer from 2 to 10; a C5–C7 cycloalkyl group or an aryl or heteroaryl group; and (c) recovering the resultant cross-linked polysaccharide.

2. A process according to claim 1 in which the carboxy-containing polysaccharide is a hyaluronic acid salified with a lipophilic cation; the solvent is selected from tetrahydrofuran, dimethylformamide or dimethyl sulfoxide; the carboxy activating agent is chloromethylpyridylium iodide and the polyamine is one in which A of the formula R$_1$NH—A-R$_2$ is a C$_2$–C$_6$ linear alkylene chain.

3. A process according to claim 2 in which the polyamine, diluted in a like solvent as used in the activation step, is added to the solution of activated poly-saccharide to effect the cross-linking reaction in 1–12 hours.

4. A process according to claim 2 in which the recovered cross-linked polysaccharide is sulphated by reaction with a pyridine-sulfur trioxide complex.

5. A process according to claim 2 in which the recovered cross-linked polysaccharide is complexed with a metal ion selected from zinc, copper and iron.

* * * * *